(12) United States Patent
Saussaye

(10) Patent No.: US 10,207,052 B2
(45) Date of Patent: Feb. 19, 2019

(54) AUTOINJECTOR

(71) Applicant: APTAR FRANCE SAS, Le Neubourg (FR)

(72) Inventor: Anthony Saussaye, Saint Sulpice sur Risle (FR)

(73) Assignee: APTAR FRANCE SAS, Le Neubourg (FR)

( * ) Notice: Subject to any disclaimer, the term of this patent is extended or adjusted under 35 U.S.C. 154(b) by 103 days.

(21) Appl. No.: 15/113,526

(22) PCT Filed: Apr. 9, 2015

(86) PCT No.: PCT/FR2015/050940
§ 371 (c)(1),
(2) Date: Jul. 22, 2016

(87) PCT Pub. No.: WO2015/155484
PCT Pub. Date: Oct. 15, 2015

(65) Prior Publication Data
US 2017/0007764 A1    Jan. 12, 2017

(30) Foreign Application Priority Data

Apr. 11, 2014 (FR) ..................... 14 53251

(51) Int. Cl.
*A61M 5/20* (2006.01)
*A61M 5/32* (2006.01)

(52) U.S. Cl.
CPC .......... *A61M 5/2033* (2013.01); *A61M 5/326* (2013.01); *A61M 2005/206* (2013.01);
(Continued)

(58) Field of Classification Search
CPC ........ A61M 2005/2073; A61M 5/2033; A61M 2005/202; A61M 2005/2026
See application file for complete search history.

(56) References Cited

U.S. PATENT DOCUMENTS 3,563,098 A * 2/1971 Gley .................... A61M 5/2033
604/135
8,945,063 B2 * 2/2015 Wotton ................ A61K 9/0019
604/181

(Continued)

FOREIGN PATENT DOCUMENTS

WO    2010/108116 A1    9/2010
WO    2013/175137 A1    11/2013
(Continued)

OTHER PUBLICATIONS

International Preliminary on Patentability Report dated Oct. 20, 2016, issued by the International Searching Authority in application No. PCT/FR2015/050940.
(Continued)

*Primary Examiner* — Nathan R Price
*Assistant Examiner* — Melissa A Snyder
(74) *Attorney, Agent, or Firm* — Sughrue Mion, PLLC

(57) ABSTRACT

An autoinjector having a piston rod for a piston of a reservoir, the piston rod movable between a primed position and an injection position; an injection spring urging the piston rod towards its injection position; and an injection lock including a control sleeve containing the piston rod and the injection spring. The piston rod includes a radial recess receiving a substantially-spherical blocking element movable between a blocking and unblocking position and urged radially outwards by the piston rod and held in its blocking position by a blocking ring; and a support member fastened in the control sleeve and having a ring with an axial end in contact with the injection spring, the other axial end supports the blocking element. The blocking ring is engaged on the support member and disengaged by the control sleeve.

17 Claims, 12 Drawing Sheets

(52) U.S. Cl.
CPC ............... *A61M 2005/2013* (2013.01); *A61M 2005/2026* (2013.01); *A61M 2205/58* (2013.01)

(56) References Cited

U.S. PATENT DOCUMENTS

2013/0317432 A1   11/2013   Fabien et al.
2015/0119812 A1    4/2015   Fabien et al.

FOREIGN PATENT DOCUMENTS

| WO | 2013/175140 A1 | 11/2013 |
|---|---|---|
| WO | 2013/175142 A1 | 11/2013 |
| WO | 2013/175144 A1 | 11/2013 |
| WO | 2013/175148 A1 | 11/2013 |

OTHER PUBLICATIONS

International Search Report for PCT/FR2015/050940 dated Jul. 20, 2015.

* cited by examiner

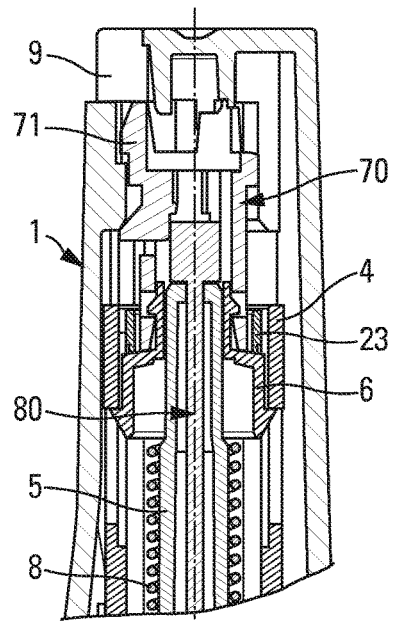
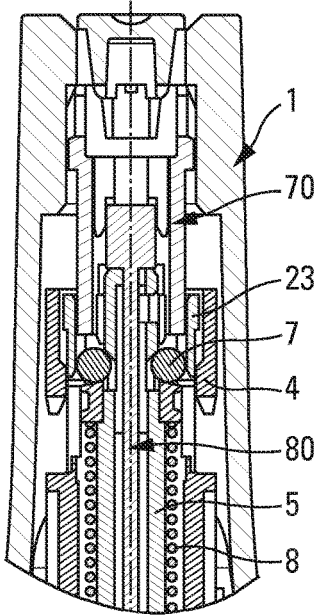
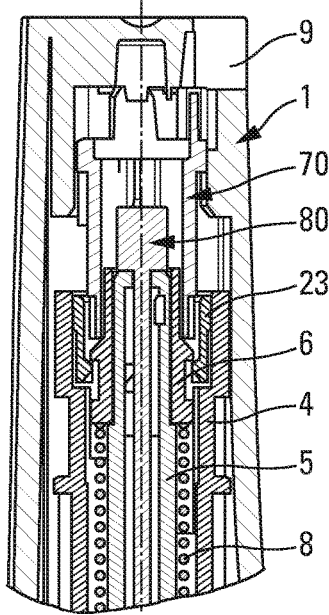
Fig. 9a  Fig. 9b  Fig. 9c
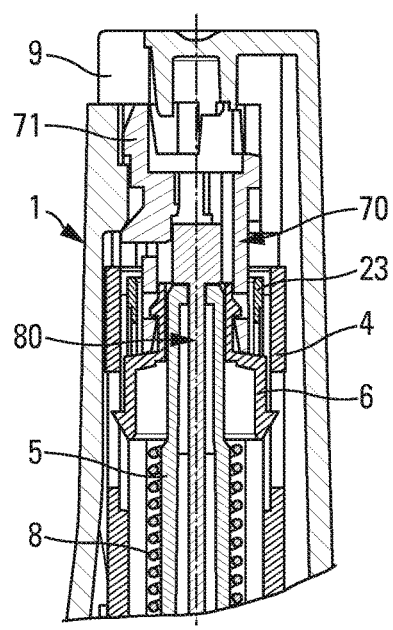
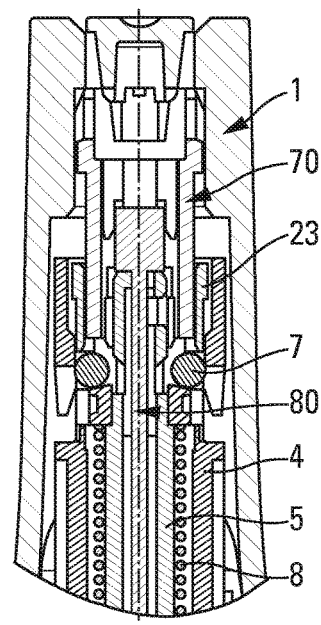
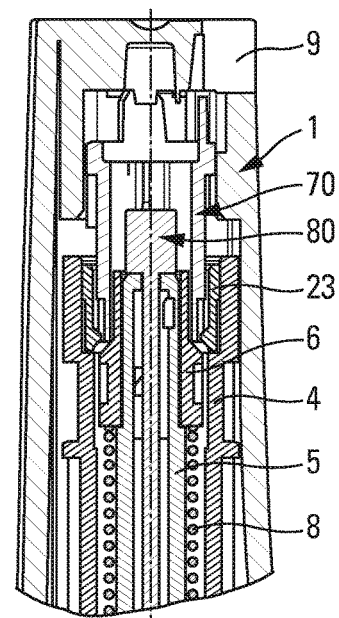
Fig. 10a  Fig. 10b  Fig. 10c

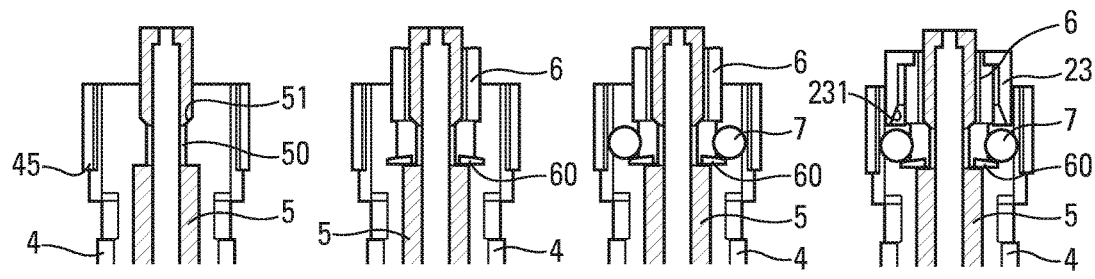
Fig. 15a  Fig. 15b  Fig. 15c  Fig. 15d
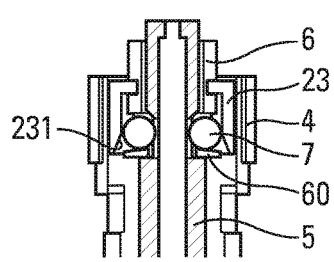 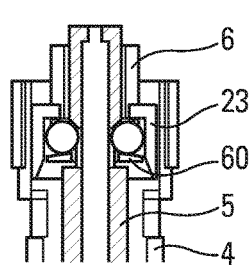 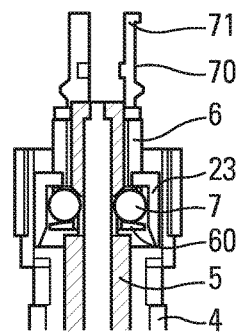
Fig. 15e  Fig. 15f  Fig. 15g
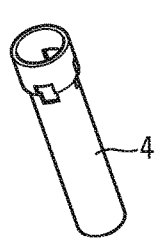 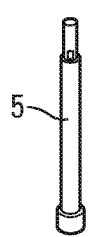 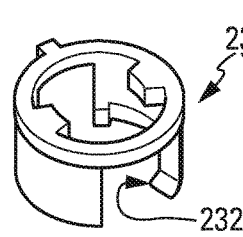 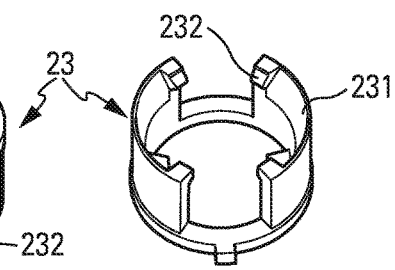
Fig. 16  Fig. 17  Fig. 18a  Fig. 18b
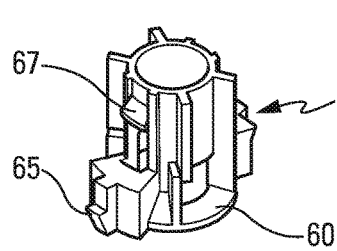 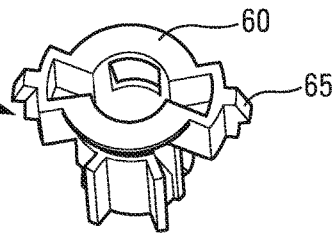 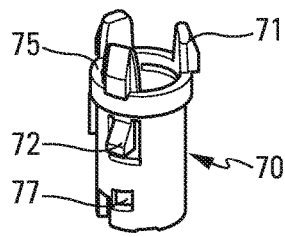
Fig. 19a  Fig. 19b  Fig. 20

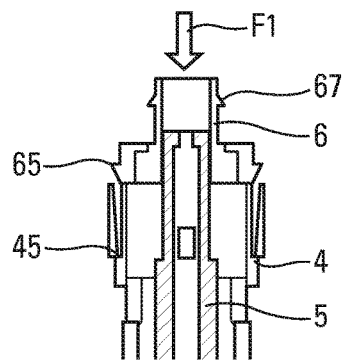
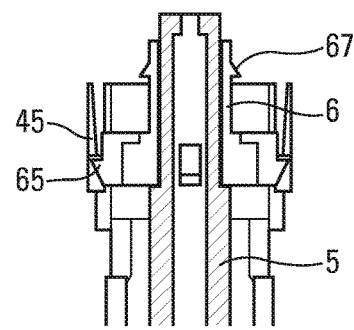
Fig. 21a　　　　Fig. 21b
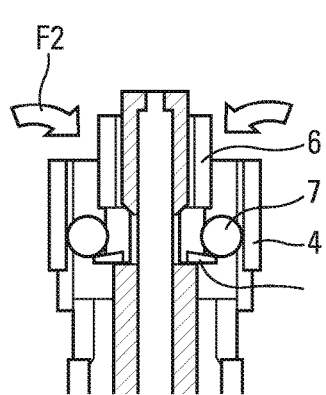
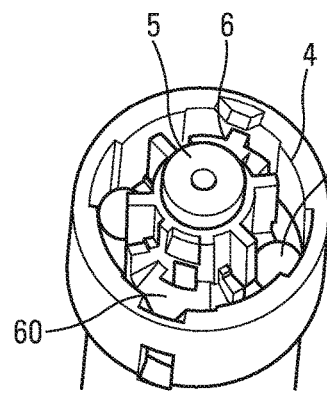
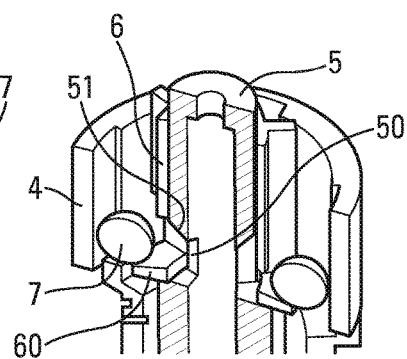
Fig. 22a　　　　Fig. 22b　　　　Fig. 22c
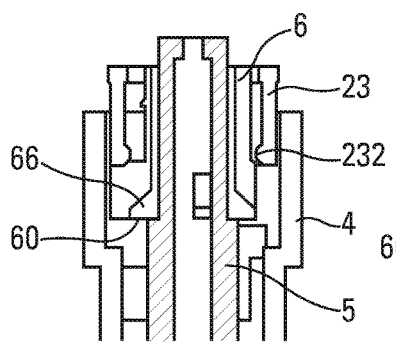
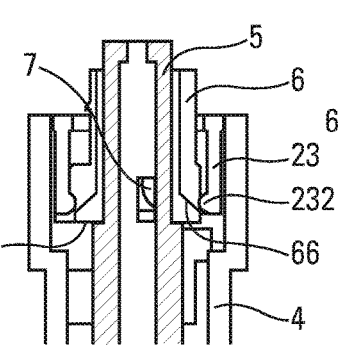
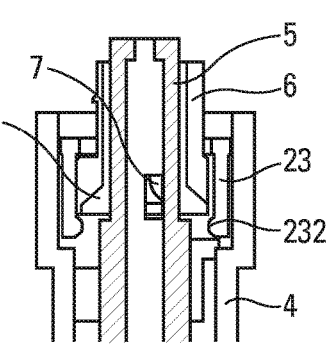
Fig. 23a　　　　Fig. 23b　　　　Fig. 23c

AUTOINJECTOR

CROSS REFERENCE TO RELATED APPLICATIONS

This application is a National Stage of International Application No. PCT/FR2015/050940 filed Apr. 9, 2015, claiming priority based on French Patent Application No. 1453251 filed Apr. 11, 2014, the contents of all of which are incorporated herein by reference in their entirety.

The present invention relates to an autoinjector.

Autoinjectors are well known in the prior art. The purpose of such devices is mainly to inject the contents of a syringe automatically into a patient's body.

Various systems exist for making the injection of the fluid contained in the syringe automatic. Autoinjectors are relatively complex devices that must satisfy a certain number of constraint requirements in order to be reliable. The robustness of the device, its handling, its reliability, and its ease of use for the user are also important elements. In addition, since most autoinjectors are for single use, the cost of manufacture and of assembly is also a factor that needs to be taken into account.

Numerous autoinjectors exist on the market, but they all present a certain number of drawbacks.

Thus, in order to avoid the autoinjector being triggered accidentally, e.g. during transport or during storage, the devices should include reliable locking means. In addition, when a user wishes to use the autoinjector and unlocks the device, e.g. by removing the cap, the device should not be triggered accidentally, but only when the user actually wishes it, i.e. when the user applies it against the part of the body where injection is to be performed. Unfortunately, in particular when the people using an autoinjector are elderly or handicapped people, the user may drop the device when it is to be used. In such circumstances, it is desirable that the autoinjector does not trigger itself. It is thus important to provide a reliable trigger lock. Equally, use of the autoinjector must not become too difficult, as this would prevent weak people from using it. It is thus difficult to find a good compromise between the safety of locking, and the ease with which the autoinjector can be used and actuated. An object of the present invention is to satisfy this problem.

Documents WO 2013/175148, WO 2013/175144, and WO 2010/108116 describe prior-art devices.

An object of the present invention is to provide an autoinjector that does not have the above-mentioned drawbacks, and that makes it possible to satisfy the various major requirements and constraints for safe and reliable use of the autoinjector.

Another object of the present invention is to provide an autoinjector that includes an injection lock that is reliable, that is able to withstand unwanted actuations, and that is easy to trigger without excessive force.

Another object of the present invention is to provide an autoinjector that is simple and inexpensive to manufacture and to assemble.

The present invention thus provides an autoinjector comprising a body that receives a reservoir, said reservoir containing fluid and including a piston and a needle, such as a pre-filled syringe, said autoinjector further comprising a piston rod that is adapted to co-operate with the piston of said reservoir, said piston rod being movable between a primed position and an injection position in which said piston rod has moved the piston of the reservoir so as to inject the fluid through the needle, an injection spring being provided for urging said piston rod towards its injection position, the autoinjector further comprising an injection lock that blocks said piston rod in its primed position, said injection lock including a control sleeve, said control sleeve containing said piston rod and said injection spring, said piston rod including a radial recess that receives at least one substantially-spherical blocking element, such as a ball, that is movable between a blocking position and an unblocking position, said at least one blocking element being urged radially outwards by said piston rod and being held in its blocking position by a blocking ring, said blocking ring being movable relative to said piston rod so as to release said at least one blocking element and thus unblock said injection lock, enabling said injection spring to move said piston rod towards its injection position, a support member being fastened, in particular snap-fastened, in said control sleeve, said support member including a ring having an axial end that is in contact with said injection spring and the other axial end supports said at least one substantially-spherical blocking element, said blocking ring being engaged, in particular snap-fastened, on said support member, said blocking ring being disengaged from said support member by said control sleeve when said control sleeve is moved axially while the autoinjector is being actuated, so as to unblock said injection lock.

Advantageously, said blocking ring includes lugs, preferably of rounded shape, that, in the blocking position of the injection lock, are snap-fastened below a sloping ramp of said support member.

Advantageously, said blocking ring includes a beveled bottom edge for urging said at least one blocking element radially inwards while said blocking ring is being assembled on said support member.

Advantageously, said support member includes first radial projections that co-operate with a shoulder of said control sleeve for fastening said support member on said control sleeve.

Advantageously, an indicator element is fastened, in particular snap-fastened, on said support member, said indicator element co-operating with the body, after injection, so as to provide the user with an audible and/or tactile and/or visual indication.

Advantageously, said support member includes second radial projections that co-operate with slots of said indicator element for fastening said indicator element on said support member.

Advantageously, said autoinjector includes an actuator sleeve that includes a contact end for coming into contact with the user's body, said actuator sleeve extending inside said body at least in part, and being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector.

Advantageously, said actuator sleeve includes a top edge that, during actuation, comes into contact with said control sleeve, such that said control sleeve is moved axially by said actuator sleeve so as to unblock said injection lock.

These characteristics and advantages, and others, of the present invention appear more clearly from the following detailed description, given by way of non-limiting example, and with reference to the accompanying drawings, in which:

FIGS. 1a and 1b are section views on two different section planes of an autoinjector in an advantageous embodiment of the present invention, before use;

FIGS. 2a and b are views similar to the views in FIGS. 1a and 1b respectively, after removing the protective cap and before actuation;

Figure 6A:
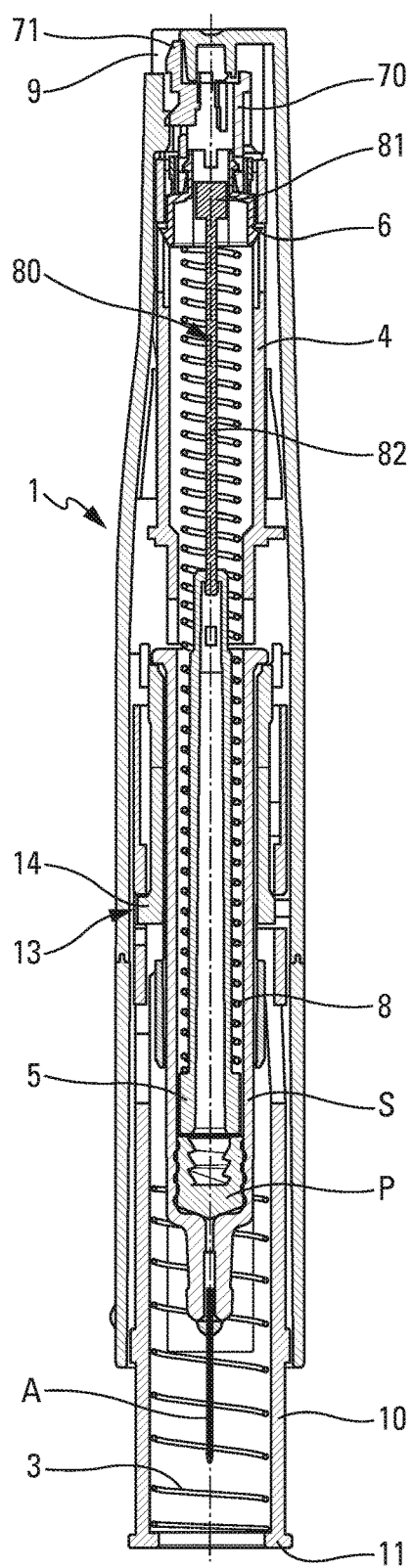
FIGS. 6a and 6b are views similar to the views in FIGS. 1a and 1b respectively, at the end of actuation.
Figure 6B:
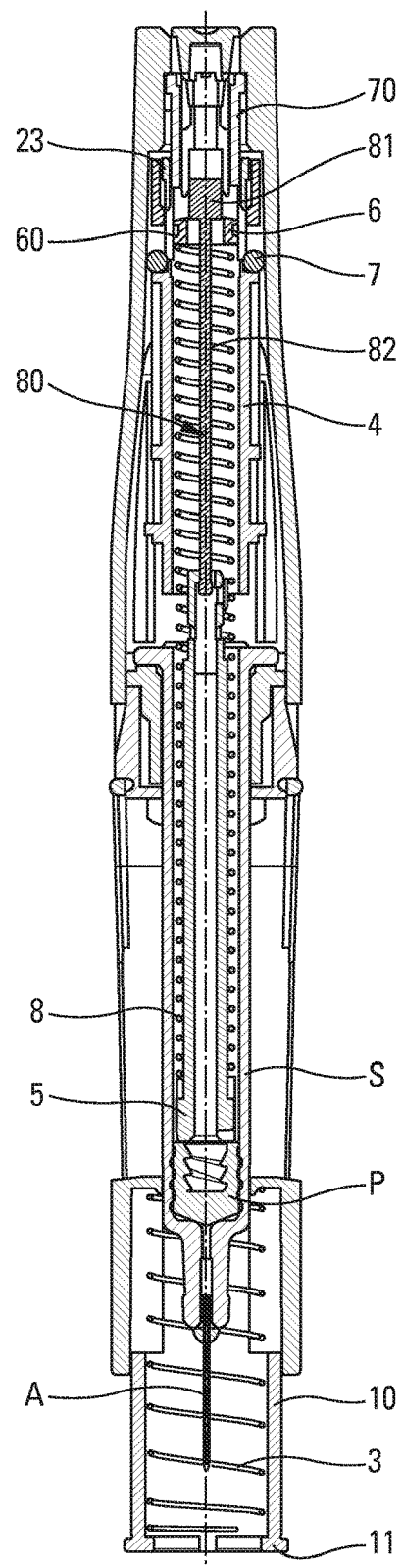
Figure 7A:
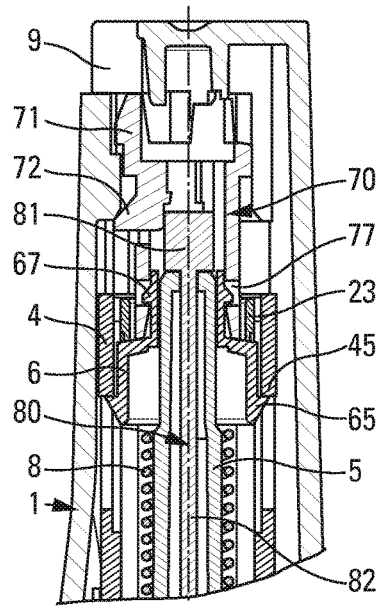
Figure 7B:
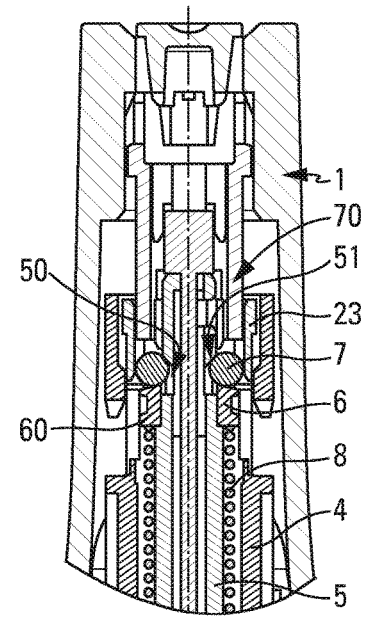
Figure 7C:
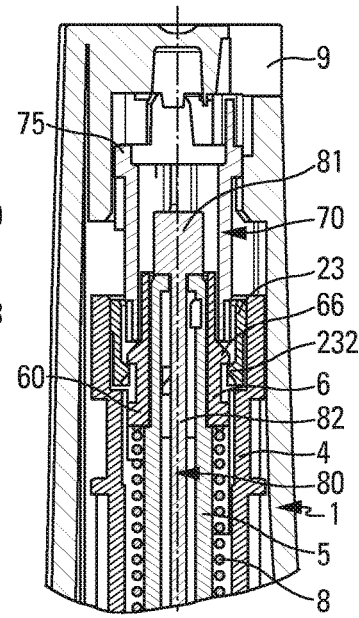
Figure 8A:
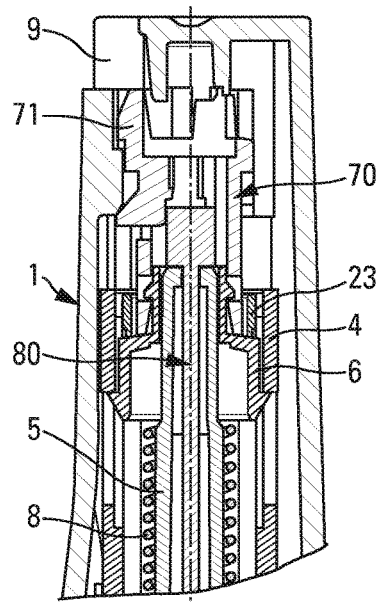
Figure 8B:
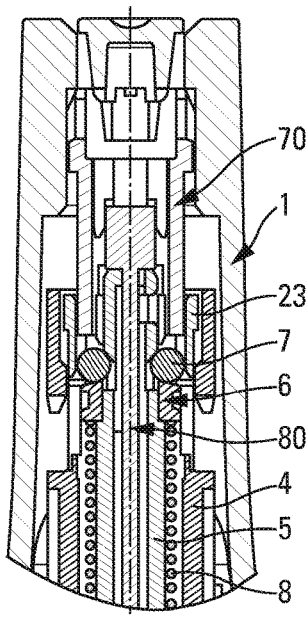
Figure 8C:
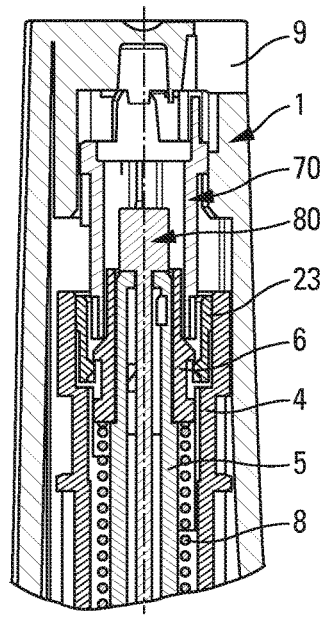
Figure 11A:
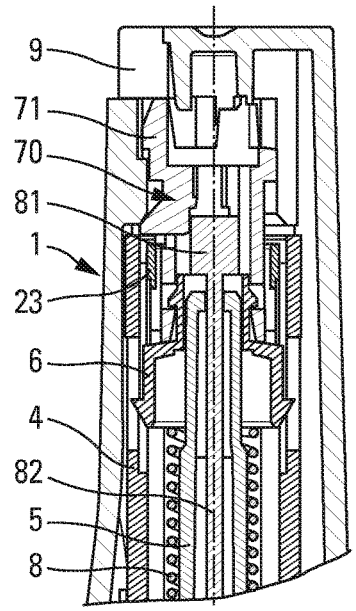
Figure 11B:
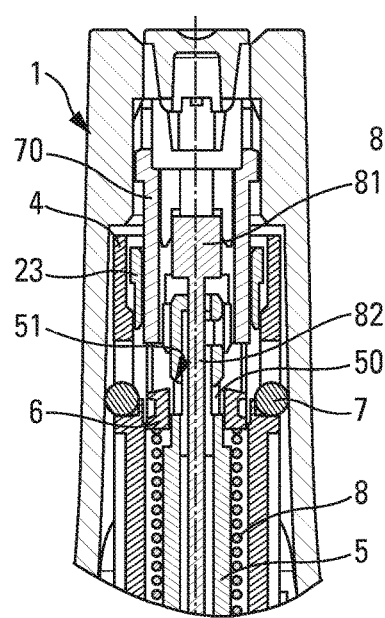
Figure 11C:
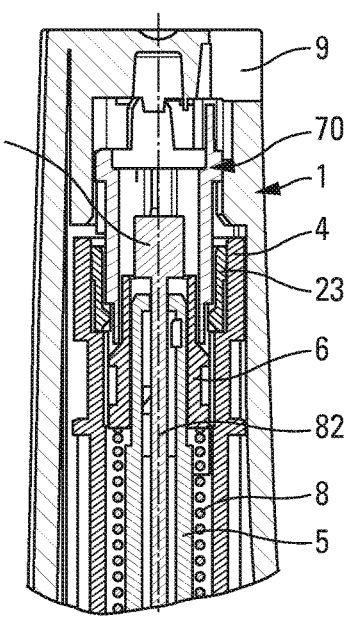
Figure 12A:
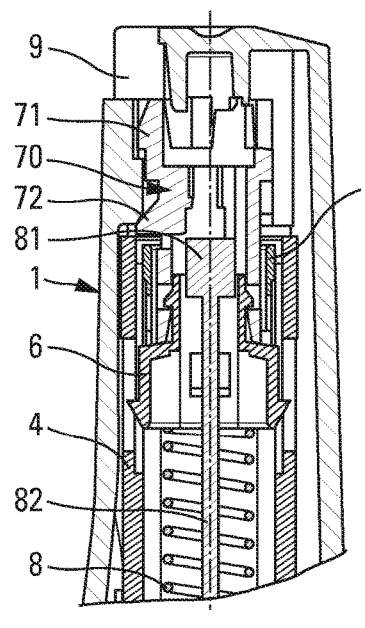
Figure 12B:
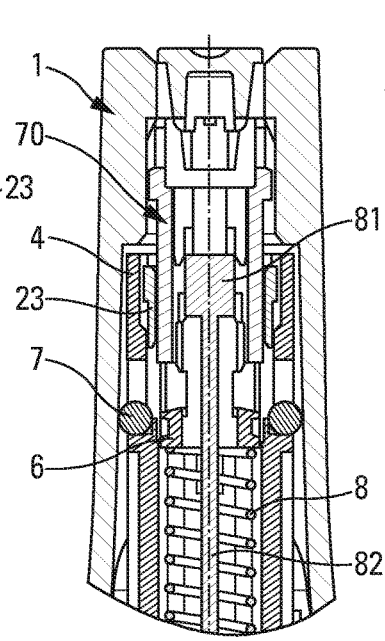
Figure 12C:
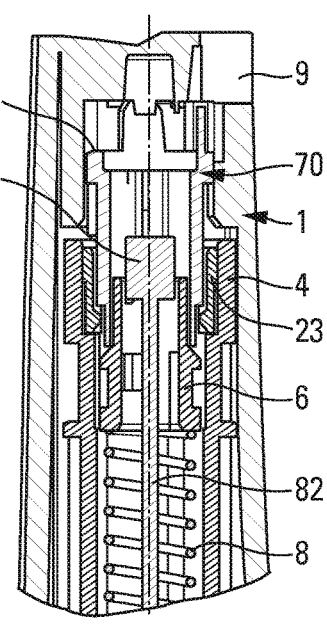
Figure 13A:
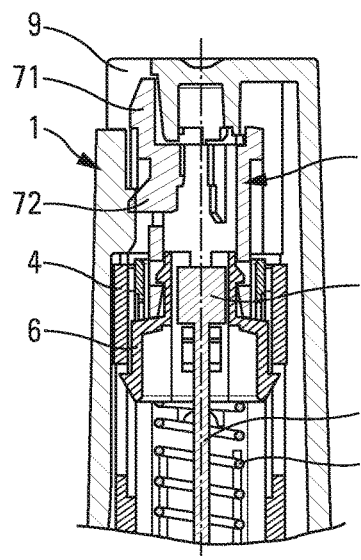
Figure 13B:
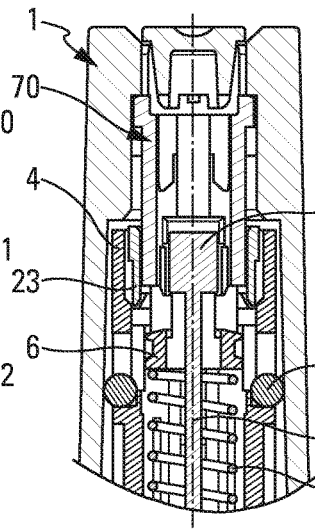
Figure 13C:
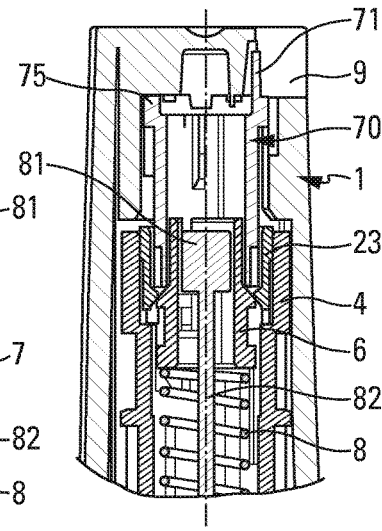
Figure 14A:
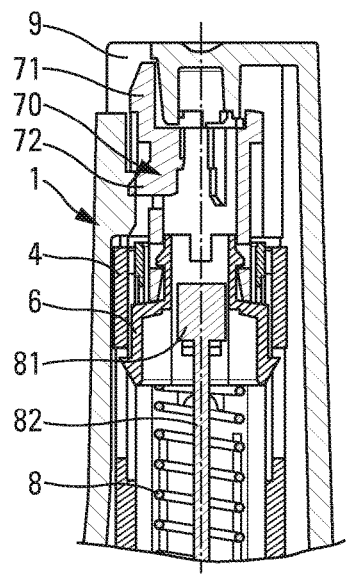
Figure 14B:
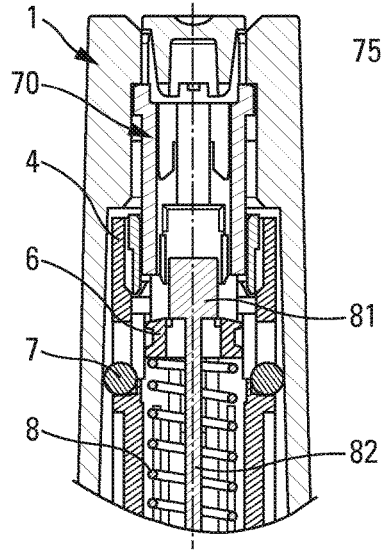
Figure 14C:
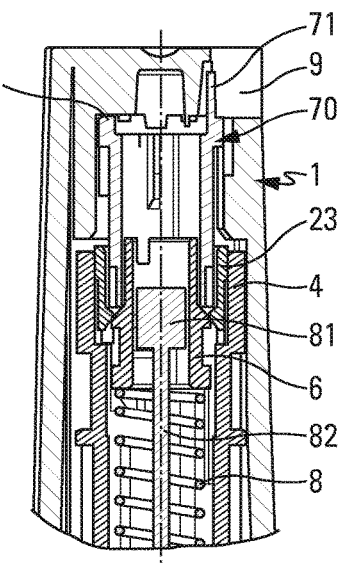

FIGS. 7a, 7b, and 7c are section views, before actuation, of a detail on three different section planes of the autoinjector in FIGS. 1 to 6, FIG. 7a and 7b being section views of a detail on the same section planes as FIGS. 1 to 6, and FIG. 7c being an additional view of a detail on another section plane not shown in FIGS. 1 to 6;

FIGS. 8a, 8b, and 8c are views similar to the views in FIGS. 7a, 7b, and 7c respectively, at the beginning of actuation;

FIGS. 9a, 9b, and 9c are views similar to the views in FIGS. 7a, 7b, and 7c respectively, before triggering the injection lock;

FIGS. 10a, 10b, and 10c are views similar to the views in FIGS. 7a, 7b, and 7c respectively, during triggering of the injection lock but before injection;

FIGS. 11a, 11b, and 11c are views similar to the views in FIGS. 7a, 7b, and 7c respectively, after triggering the injection lock at the beginning of injection;

FIGS. 12a, 12b, and 12c are views similar to the views in FIGS. 7a, 7b, and 7c respectively, at the end of injection but before triggering the end of injection indicator;

FIGS. 13a, 13b, and 13c are views similar to the views in FIGS. 7a, 7b, and 7c respectively, at the end of injection but after triggering the end of injection indicator;

FIGS. 14a, 14b, and 14c are views similar to the views in FIGS. 7a, 7b, and 7c respectively, after injection;

FIGS. 15a to 15g are diagrammatic detail views of the assembly sequences of the injection lock;

FIG. 16 is a diagrammatic perspective view of the control sleeve of the autoinjector in FIGS. 1 to 14;

FIG. 17 is a diagrammatic perspective view of the piston rod of the autoinjector in FIGS. 1 to 14;

FIGS. 18a and 18b are diagrammatic perspective views on two different orientations of the blocking ring of the autoinjector in FIGS. 1 to 14;

FIGS. 19a and 19b are diagrammatic perspective views on two different orientations of the support member of the autoinjector in FIGS. 1 to 14;

FIG. 20 is a diagrammatic perspective view of the indicator element of the autoinjector in FIGS. 1 to 14;

FIGS. 21a and 21b are diagrams showing the assembly of the support member in the control sleeve, in the embodiment in FIGS. 1 to 14;

FIGS. 22a to 22c are diagrams showing the blocking elements of the injection lock being assembled, in the embodiment in FIGS. 1 to 14; and FIGS. 23a to 23c are diagrams showing the blocking ring assembled on the support member, in the embodiment in FIGS. 1 to 14.

In the following description, the terms "top", "bottom", "high", and "low" refer to the positions shown in FIGS. 1a to 15g and 21a to 23c. The terms "axial" and "radial" refer to the longitudinal central axis X shown in particular in FIG. 1a.

The autoinjector is described below with reference to an advantageous embodiment. It should nevertheless be observed that autoinjectors, which are complex appliances, comprise a plurality of modules for performing a plurality of functions. The various modules may be used separately and independently of one another, without necessarily being combined with the other modules, and in particular they could be used in autoinjectors of shape that is different from the shape shown in the drawings. Furthermore, it should be observed that the drawings are diagrammatic views, which do not necessarily represent the exact shape of the components of an autoinjector, and they are not necessarily to scale, in particular for purposes of clarity. In addition, the drawings do not necessarily represent all of the component elements of an autoinjector, but only the elements necessary for operation of the present invention. Thus, various additional and/or complementary elements and modules could be associated with the autoinjector shown in the figures.

Figure 1A:
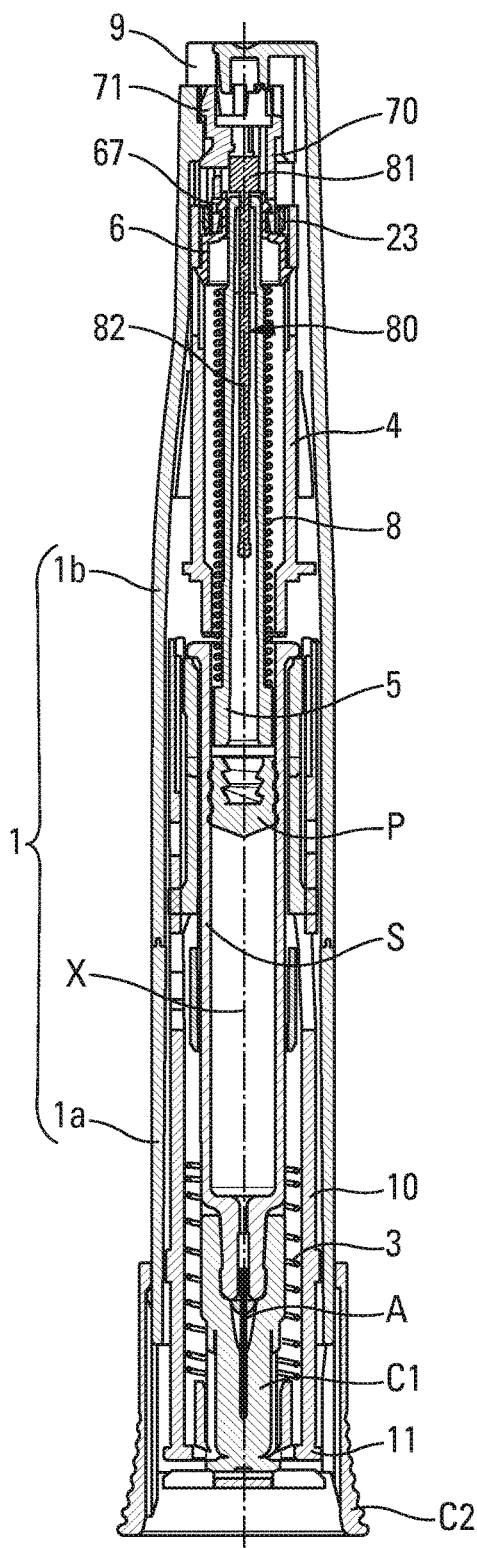
Figure 1B:
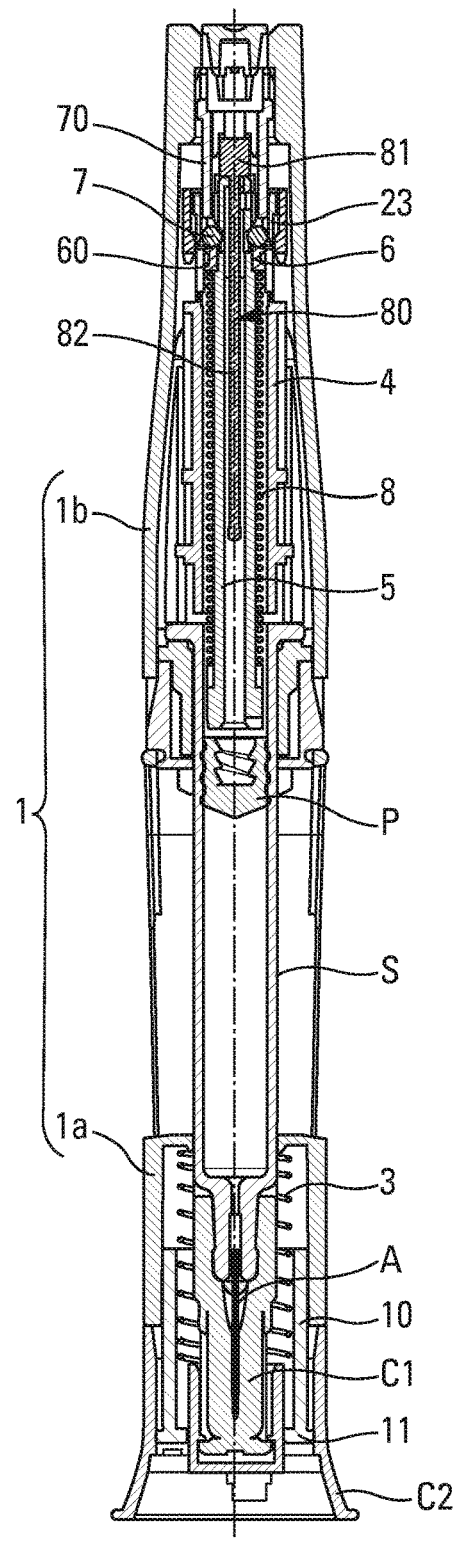

The autoinjector shown in the figures comprises a body 1 in which an actuator sleeve 10 slides axially, the actuator sleeve 10 having a bottom end 11 that is for coming into contact with the body of the patient around the injection zone. In the embodiment shown in the figures, the autoinjector includes a lower body 1a and an upper body 1b that are assembled together so as to form the body 1 of the autoinjector, as indicated in FIGS. 1a and 1b. Below, and in the other figures, the term "body" and the numerical reference "1" are used to designate said unitary body formed by assembling said lower body 1a with said upper body 1b.

A reservoir S may be inserted into said autoinjector. The reservoir S contains fluid and includes a piston P and a needle A. The piston P is adapted to move in said reservoir S so as to inject the fluid through said needle A.

The present description is made with reference to a syringe S that may be of any type. More generally, it is understood that the term "syringe" in the present description encompasses any type of reservoir associated with a needle. Preferably, the reservoir S is a pre-filled syringe.

Before the autoinjector is actuated, the needle A of the syringe S is preferably protected by a guard C1, the autoinjector including a cap C2 that the user can remove before actuation. Removal of the cap C2 causes the guard C1 to be removed.

Figure 2A:
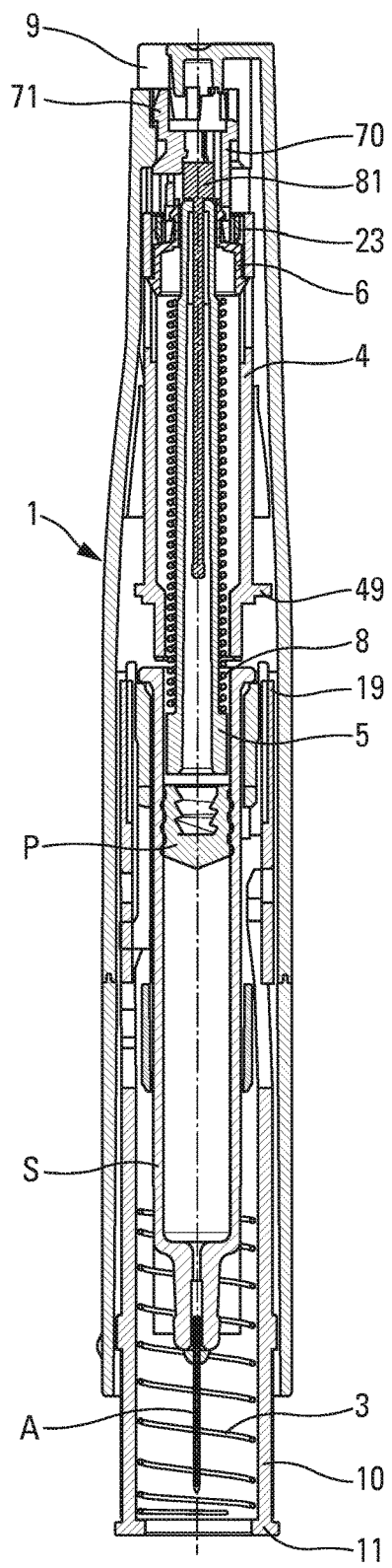
Figure 2B:
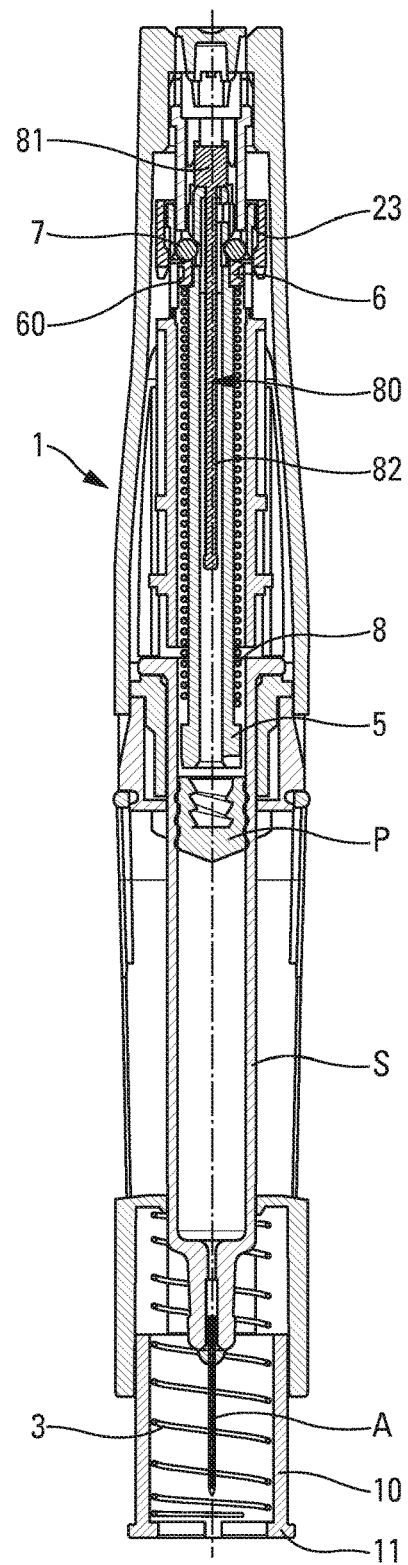

Before actuation, the actuator sleeve 10 is in a first projecting position in which it surrounds the needle A, as shown in FIGS. 2a and 2b. During actuation, the actuator sleeve 10 slides inside the body 1 towards an actuated position, so as to expose the needle A and enable pricking, and then injection of the fluid. After injection, the actuator sleeve 10 returns into a second projecting position in which it is once again arranged around the needle A, so as to avoid any risk of injury with said needle, as shown in FIGS. 6a and 6b. The actuator sleeve 10 is advantageously urged towards its projecting positions by a spring 3 that may be of any type. Advantageously, in said second projecting position after injection, said actuator sleeve 10 is locked, and can no longer be moved axially into said body 1. By way of example, locking may be achieved by tabs 14 that are secured to the body 1 or to the reservoir S, and that co-operate with openings 13 in said actuator sleeve 10 when said actuator sleeve reaches its second projecting position. In the embodiment shown, the tabs 14 are secured to the reservoir S, as can be seen in particular in FIGS. 5a and 6a. Locking, that is not essential to the operation of the present invention, is not described in greater detail below. It could be achieved in ways that are different to the particular embodiment shown in the drawings. In particular, it could be achieved in accordance with the teaching of documents WO 2013/175140 or WO 2013/175142.

The autoinjector also includes an automatic injection system, in particular comprising a piston rod 5 that is adapted to co-operate with the piston P so as to move it in the reservoir S so as to dispense the fluid through the needle A. Conventionally, the piston rod 5 is urged by an injection spring 8 towards its dispensing position and, before actuation, it is held in its rest position by an appropriate injection lock.

FIGS. 1a to 14c are diagrams showing an advantageous injection lock of the invention, which injection lock includes at least one blocking element 7 that is held in its blocking position by a blocking ring 23. Triggering said injection lock causes said injection means to be actuated, and thus fluid to be injected through the needle.

As shown in particular in FIG. 7b, said injection lock includes a control sleeve 4 that is arranged in said body 1, said control sleeve 4 containing said piston rod 5 and said injection spring 8, said piston rod 5 including a radial recess 50 that receives at least one blocking element 7 that is movable between a blocking position and an unblocking position. Said at least one blocking element 7 is preferably of shape that is substantially spherical, such as a ball. In the variant shown, there are two blocking elements 7 in the form of balls, but a different number of blocking elements may be envisaged. Reference is made below to balls as blocking elements 7. Said balls 7 are urged radially outwards by said piston rod 5 and they are held in their blocking position by the blocking ring 23. The blocking ring 23 is axially movable relative to said piston rod 5 between a locking position in which it holds said balls 7 in their blocking position, and an unlocking position in which said balls 7 are released, thus unblocking said injection lock and enabling said injection spring 8 to move said piston rod 5 towards its injection position.

FIGS. 7a to 9c show the injection lock in the blocking position. The injection spring 8 co-operates firstly with the piston rod 5, and secondly with a support member 6. The support member 6 comprises a ring 60 that is arranged around said piston rod 5. The piston rod 5 includes a peripheral recess 50 that is advantageously provided with a sloping surface 51, and that is formed by a constriction of the diameter of said piston rod 5. This can be seen more clearly in FIGS. 11b and 15a. The piston rod 5 is arranged inside the control sleeve 4 and is suitable for being moved axially downwards, in the positions shown in FIGS. 1a to 15g, so as to move the piston P inside the syringe S and thus dispense the fluid contained in said syringe S through the needle A.

As can be seen in particular in FIG. 7b and in FIGS. 15f and 15g, in the blocking position of the injection lock, the balls 7 are arranged in said recess 50 formed in the piston rod 5, and thus co-operate firstly with the sloping wall 51 of the piston rod 5, secondly with the top surface of said ring 60 of said support member 6, and also with said blocking ring 23.

The sloping surface 51 of the piston rod is in contact with the balls 7 so that under the effect of the compressed spring 8, said sloping surface 51 exerts a reaction force on the balls 7, this force not being exactly axial, but directed outwards a little, thereby urging the balls 7 radially outwards from the FIG. 20 blocking position.

The blocking ring 23 is provided radially outwards from the balls 7 so as to block said balls radially in the blocking position.

The support member 6 transmits the force of the spring 8 to the balls 7, and the blocking ring 23 exerts a reaction force on the balls 7 so as to prevent said balls from moving radially. Thus, the balls 7 support all of the forces exerted on the lock in the blocking position, with three-point balance under the effect of the three above-mentioned forces. Such a lock is particularly stable and robust, and in particular makes it possible to withstand drop tests. Such tests simulate dropping the autoinjector onto the floor after removing the cap C2, the purpose being to avoid triggering the injection lock when dropped. In particular, no force is exerted on the structural parts of the autoinjector, such as the body 1 or the actuator sleeve 10. The lock thus makes it possible to avoid a risk of the autoinjector being disassembled and/or accidentally actuated during transport or handling.

When the needle A of the syringe S has penetrated the user's body, the blocking ring 23 is moved axially upwards, as described more fully below. This causes the balls 7 to be released from their blocking position, said balls then moving radially outwards. The piston rod 5 is then no longer held by the balls 7, and it is thus moved axially downwards so as to inject the fluid. After triggering the injection lock, the balls 7 can no longer return radially inwards, since they are prevented by the control sleeve 4, as can be seen in FIGS. 11b, 12b, 13b, and 14b.

The injection lock shown in the figures makes it possible to release a significant force as exerted by a compressed spring, specifically the injection spring 8, by exerting a relatively small and easily controllable force on the blocking ring 23. In particular, the force necessary to move said blocking ring 23 into its unblocking position may represent only 30% to 50%, or less, of the force exerted by the injection spring 8. This represents a significant gain that guarantees easy and reliable actuation of the device, without requiring excessive force from the user.

Advantageously, the autoinjector includes a visual, audible, and/or tactile indicator device for indicating to the user, by an audible sound, by vibration, or by visual and/or tactile indication, that the injection stage has ended.

In the embodiment shown, the indicator device comprises an indicator element 70 that is secured to the support member 6 against which the injection spring 8 bears. FIG. 20 shows the indicator element that includes one or more tabs 71, specifically three tabs. Operation is similar to the device described in document WO 2014/049214, with a key 80 comprising a head 81 and a rod 82, said head blocking the radial deformation of a deformable tab 72 that is formed on the indicator element 70, and this blocks the indicator element 70 relative to the body 1. In the variant shown, there is a single deformable tab 72, but a different number of deformable tabs could be envisaged. At the end of injection, the piston rod 5 causes said key 80 to slide axially downwards by applying traction on said rod 82, such that said head 81 of the key 80 releases said deformable tab 72 that, by deforming radially inwards, enables an edge portion 75 of said indicator element 70 to be projected against said body 1, under the effect of an injection spring 8, creating an audible and/or tactile indication, in particular by causing the autoinjector to vibrate. FIGS. 13c and 14c show, in particular, the contact between the edge portion 75 of the indicator element 70 and the body 1. Advantageously, a visual indication is also provided via one or more viewing slots 9 of the body 1, specifically three in this embodiment, which show the tabs 71 of the indicator element 70.

Figure 3A:
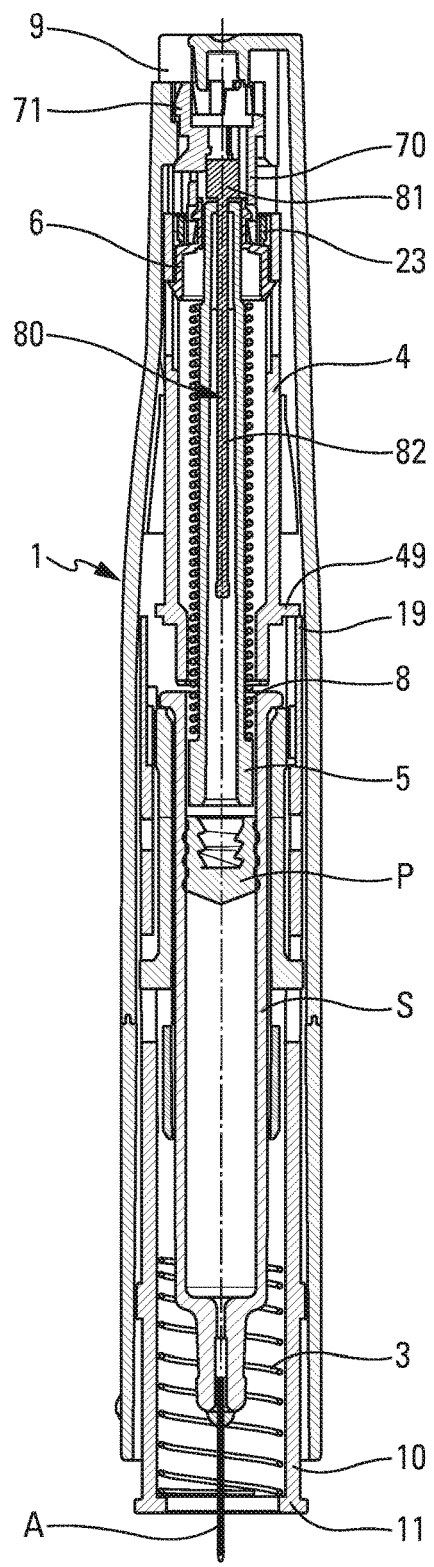
FIGS. 3a and 3b are views similar to the views in FIGS. 1a and 1b respectively, at the beginning of actuation.
Figure 3B:
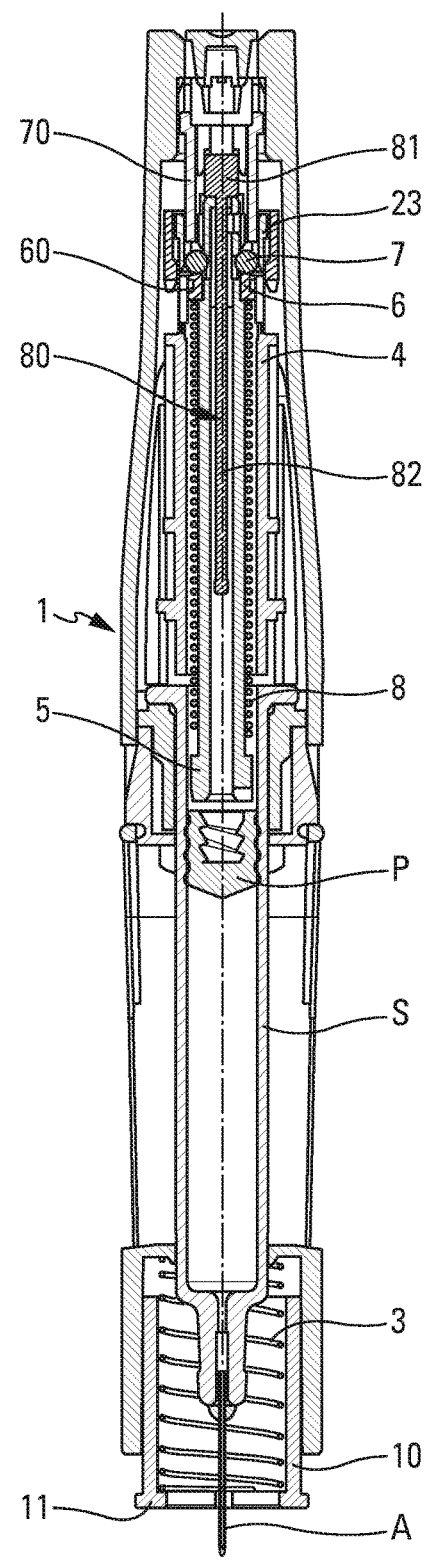
Figure 4A:
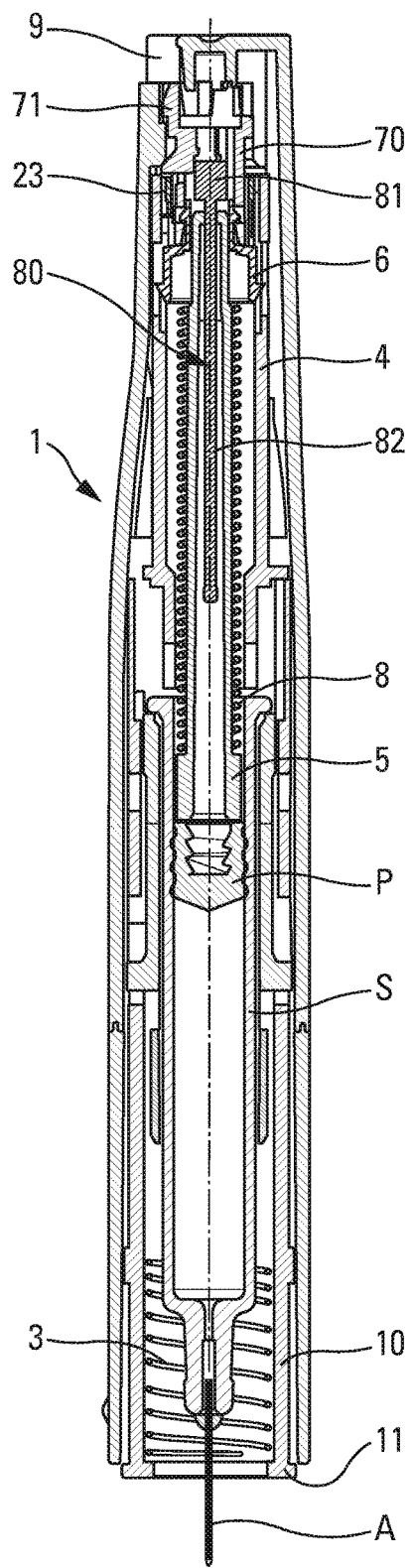
FIGS. 4a and 4b are views similar to the views in FIGS. 1a and 1b respectively, during actuation and at the beginning of injection.
Figure 4B:
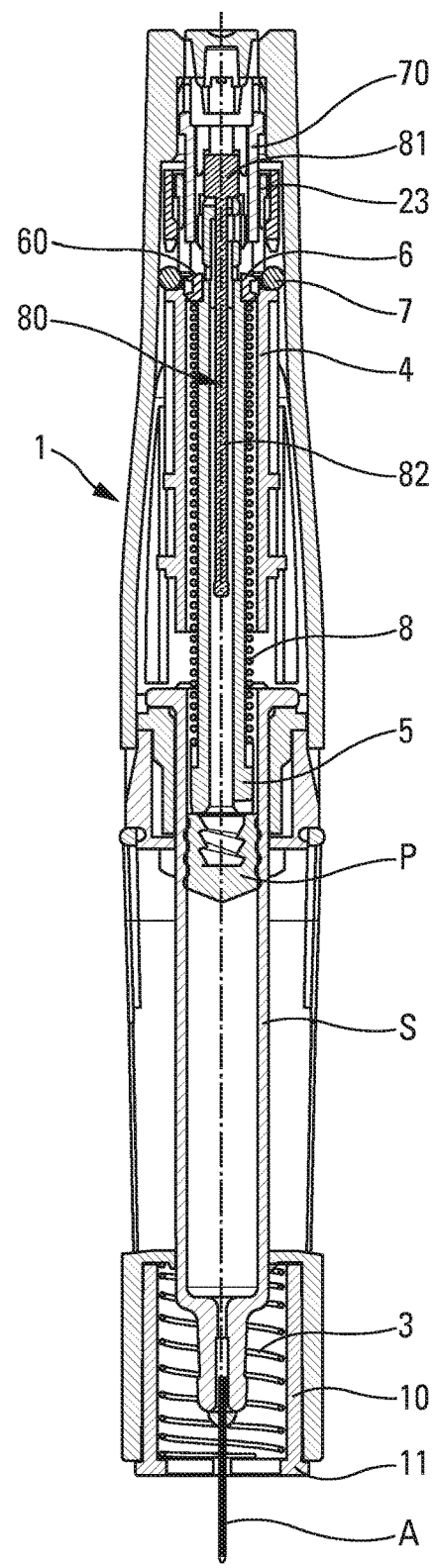
Figure 5A:
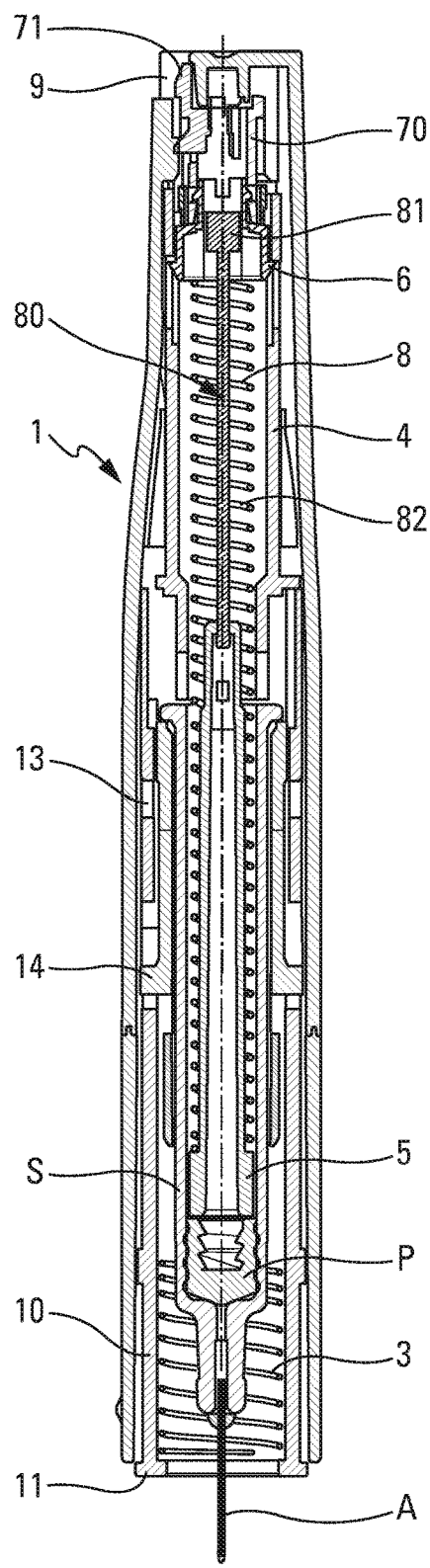
FIGS. 5a and 5b are views similar to the views in FIGS. 1a and 1b respectively, after injection.
Figure 5B:
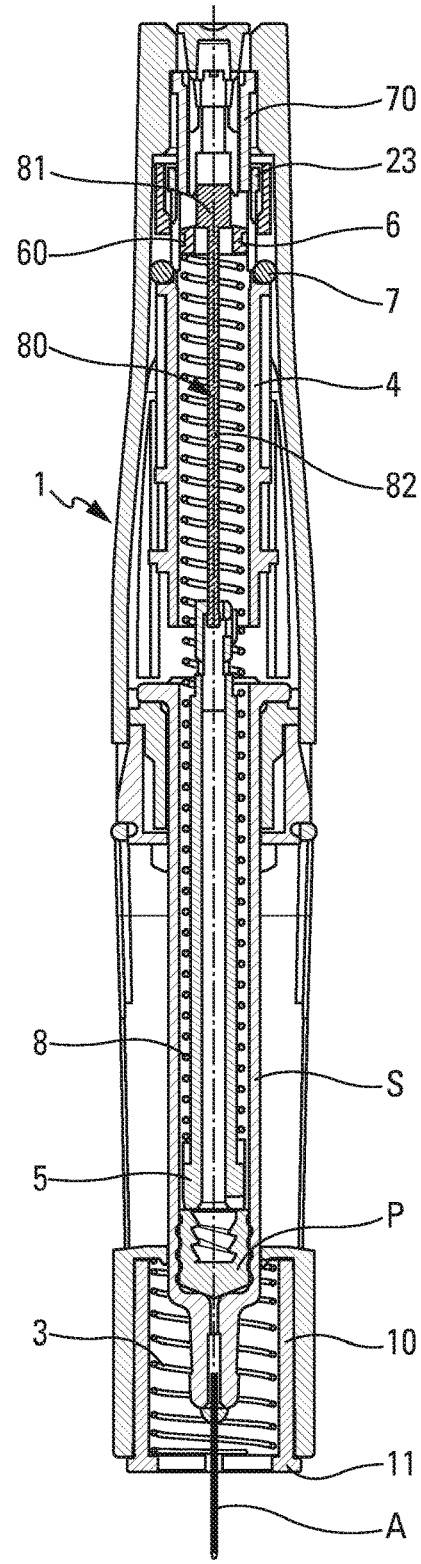

The injection lock operates as follows. After removing the cap C2 and guard C1, the autoinjector is ready to be used. This initial position is shown in FIGS. 2a and 2b, and in FIGS. 7a to 7c. At the beginning of actuation, the actuator sleeve 10 slides into the body, and a top end 19 of the actuator sleeve 10 comes into contact with a shoulder 49 of the control sleeve 4, as shown in FIG. 3a. When this contact between the actuator sleeve 10 and the control sleeve 4 is made, a small gap exists between the bottom edge of the blocking ring 23 and the control sleeve 4, as can be seen in FIG. 8c. Continued axial sliding of the actuator sleeve 10 thus drives the control sleeve 4 axially upwards, and this leads to contact between the control sleeve 4 and the blocking ring 23, as can be seen in FIG. 9c. In this position, the injection lock is still in its blocking position. Continued axial movement of the actuator sleeve 10 thus moves said blocking ring 23 axially upwards, via said control sleeve 4. This movement of the blocking ring releases the balls 7 so as to trigger the injection lock. As can be seen in FIGS. 4a, 4b, and 10a to 10c, once the bottom edge of the blocking ring 23 is no longer in contact with the balls 7, said balls can escape radially outwards, thereby releasing the piston rod 5. In this position, the injection lock no longer blocks the piston rod 5, and injection begins under the effect of the injection spring 8. As can be seen in FIG. 11b, the balls 7 become positioned in a slot of the control sleeve 4. When the piston P comes towards the end of the injection stroke, as shown in the FIGS. 5a and 5b, the piston rod 5 co-operates with the rod 82 of the key 80, so as to pull said rod axially downwards. As a result, the head 81 of the key also moves axially downwards, as shown in FIGS. 12a to 12c, and this releases the indicator element 70. When the head 81 of the key 80 no longer blocks the indicator element 70, as can be seen in FIGS. 13a to 13c, said indicator element is moved axially upwards under the effect of the injection spring 8 that bears against the support member 6, itself secured to said indicator element 70. This causes an audible and/or tactile indication by sudden contact between the indicator element 70 and the body 1, and a visual indication by the tabs 71 that can now be seen in the slots 9 of the body 1. When the injection stage has ended, the spring 3 urges the actuator sleeve 10 towards its second projecting position so as to cover the needle A, as can be seen in FIGS. 6a and 6b.

FIGS. 15a to 15g show the injection lock being assembled.

The piston rod 5 is arranged in the control sleeve 4, then the support member 6 is arranged in said control sleeve 4 around said piston rod 5. FIGS. 7a, 21a, and 21b show first radial projections 65 of the support member 6 being snap-fastened below a shoulder 45 of the control sleeve 4, when the support member 6 is moved axially downwards in the direction of arrow F1.

Then, the balls 7 are put in place via the top, along arrows F2 in FIG. 22a, becoming positioned inside the control sleeve 4, on the ring 60 of the support member 6.

Then, the blocking ring 23 is assembled in said control sleeve 4, around said support member 6. The blocking ring 23 advantageously includes a beveled bottom portion 231 that pushes the balls radially inwards while the blocking ring 23 is being assembled, as shown in FIG. 15e. In this way, the balls come into their blocking position, in the recess 50 of the piston rod 5, in contact against said sloping wall 51 of the piston rod 5. As can be seen in FIGS. 7c, and 23a to 23c, the blocking ring 23 includes lugs 232 that project radially inwards and that, during assembly, become engaged, in particular by snap-fastening, below a sloping ramp 66 of the support member 6. While triggering the injection lock, the blocking ring 23 becomes disengaged from the support member 6 so as to release the balls 7. The lugs 232, preferably of rounded shape, reinforce the ability of the lock to withstand drop tests, preventing said blocking ring 23 from moving out from its blocking position in unwanted manner. Another advantage of the blocking ring 23 is to create a point of resistance during actuation, in particular via the snap-fastening of the lugs 232. This "hard point", which must be overcome during actuation, makes it possible to guarantee that the patient is pricked fully, in order to inject at the correct depth. This "hard point" is also positioned so as to provide an initial dead stroke of the actuator sleeve 10, until the control sleeve 4 comes into contact with the blocking ring 23, thus enabling the user to make several attempts at positioning the autoinjector before triggering injection.

In the positions in FIGS. 15f and 23c, the injection lock is in its blocking position. Then, the indicator element 70 is assembled on the support member 6, via slots 77 that co-operate with second radial projections 67 of the support member 6, as can be seen in particular in FIG. 7a.

The present invention applies to devices used in particular for treatment of auto-immune diseases, e.g. of the rheumatoid arthritis, multiple scleroses, Crohn's disease type, for treatment of cancer, for antiviral treatments, e.g. of the hepatitis type, for treatment of diabetes, for treatment of anemia, or for treatment of allergy attacks, e.g. in the event of anaphylactic shock.

Although the present invention is described above with reference to an advantageous embodiment, naturally various modifications are possible for the person skilled in the art, without going beyond the ambit of the present invention, as defined by the accompanying claims.

The invention claimed is:

1. An autoinjector comprising a body that receives a reservoir, said reservoir containing fluid and including a piston and a needle, said autoinjector further comprising a piston rod that is adapted to co-operate with the piston of said reservoir, said piston rod being movable between a primed position and an injection position in which said piston rod has moved the piston of the reservoir so as to inject the fluid through the needle, an injection spring being provided for urging said piston rod towards its injection position, the autoinjector further comprising an injection lock that blocks said piston rod in its primed position, said injection lock including a control sleeve, said control sleeve containing said piston rod and said injection spring, said piston rod including a radial recess that receives at least one substantially-spherical blocking element that is movable between a blocking position and an unblocking position, said at least one blocking element being urged radially outwards by said piston rod and being held in its blocking position by a blocking ring, said blocking ring being movable relative to said piston rod so as to release said at least one blocking element and thus unblock said injection lock, enabling said injection spring to move said piston rod towards its injection position, wherein a support member is fastened to said control sleeve, said support member including a ring having an axial end that is in contact with said injection spring and the other axial end supports said at least one substantially-spherical blocking element, said blocking ring being engaged to said support member, said blocking ring being disengaged from said support member by said control sleeve when said control sleeve is moved axially while the autoinjector is being actuated, so as to unblock said injection lock.

2. An autoinjector according to claim 1, wherein said blocking ring includes lugs that, in the blocking position of the injection lock, are snap-fastened below a sloping ramp of said support member.

3. An autoinjector according to claim 1, wherein said blocking ring includes a beveled bottom edge for urging said at least one blocking element radially inwards while said blocking ring is being assembled on said support member.

4. An autoinjector according to claim 1, wherein said support member includes first radial projections that co-operate with a shoulder of said control sleeve for fastening said support member on said control sleeve.

5. An autoinjector according to claim 1, wherein an indicator element is fastened on said support member, said indicator element co-operating with the body, after injection, so as to provide the user with an audible and/or tactile and/or visual indication.

6. An autoinjector according to claim 5, wherein said support member includes second radial projections that co-operate with slots of said indicator element for fastening said indicator element on said support member.

7. An autoinjector according to claim 1, wherein said autoinjector includes an actuator sleeve that includes a contact end for coming into contact with the user's body, said actuator sleeve extending inside said body at least in part, and being movable relative to said body between projecting positions in which said actuator sleeve projects out from said body at least in part, and an actuated position in which said actuator sleeve is moved axially into said body, said actuator sleeve being in a first projecting position before actuation of the autoinjector, and in a second projecting position after actuation of the autoinjector.

8. An autoinjector according to claim 7, wherein said actuator sleeve includes a top edge that, during actuation, comes into contact with said control sleeve, such that said control sleeve is moved axially by said actuator sleeve so as to unblock said injection lock.

9. The autoinjector according to claim 1, wherein the piston and needle form a pre-filled syringe.

10. The autoinjector according to claim 1, wherein the at least one substantially-spherical blocking element is a ball.

11. The autoinjector according to claim 1, wherein the support member is snap-fastened to the control sleeve.

12. The autoinjector according to claim 1, wherein the blocking ring is snap-fastened to the support member.

13. The autoinjector according to claim 5, wherein the indicator element is snap-fastened to the support member.

14. The autoinjector according to claim 1, wherein the engagement of the blocking ring to the support member provides resistance against disengagement of the blocking ring from the support member during actuation of the autoinjector, the resistance aiding in injection of the needle.

15. The autoinjector according to claim 1, wherein the ring of the support member, in which one axial end contacts the injection spring and the other axial end supports the at least one substantially-spherical blocking element, is a one-piece integral construction and the axial end that supports the at least one substantially-spherical blocking element directly contacts the at least one substantially-spherical blocking element.

16. The autoinjector according to claim 2, wherein the lugs are of rounded shape.

17. The autoinjector according to claim 1, wherein the support member is fastened in the control sleeve.

* * * * *